(12) United States Patent
Wimberger-Friedl et al.

(10) Patent No.: US 10,393,634 B2
(45) Date of Patent: Aug. 27, 2019

(54) CARTRIDGE AND APPARATUS FOR PREPARING A BIOLOGICAL SAMPLE

(71) Applicant: KONINKLIJKE PHILIPS N.V., Eindhoven (NL)

(72) Inventors: Reinhold Wimberger-Friedl, Veldhoven (NL); Freek Van Hemert, Dordrecht (NL); Anja Van De Stolpe, Vught (NL); Menno Willem Jose Prins, Rosmalen (NL); Johannes Adrianus Van Tooren, Arnhem (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 22 days.

(21) Appl. No.: 14/651,859

(22) PCT Filed: Sep. 24, 2013

(86) PCT No.: PCT/IB2013/058789
§ 371 (c)(1),
(2) Date: Jun. 12, 2015

(87) PCT Pub. No.: WO2014/091321
PCT Pub. Date: Jun. 19, 2014

(65) Prior Publication Data
US 2015/0316454 A1 Nov. 5, 2015

Related U.S. Application Data

(60) Provisional application No. 61/736,697, filed on Dec. 13, 2012.

(51) Int. Cl.
*G01N 1/00* (2006.01)
*G01N 1/31* (2006.01)
*B01L 3/00* (2006.01)

(52) U.S. Cl.
CPC ........ *G01N 1/312* (2013.01); *B01L 3/502715* (2013.01); *B01L 3/523* (2013.01);
(Continued)

(58) Field of Classification Search
CPC ....................................................... G01N 1/28
See application file for complete search history.

(56) References Cited

U.S. PATENT DOCUMENTS 7,141,386 B2 * 11/2006 Dunfield ................. C12M 29/06
435/30
7,932,098 B2 * 4/2011 Childers ........... B01L 3/502707
436/174

(Continued)

FOREIGN PATENT DOCUMENTS

JP    2008196943 A    8/2008
RU    2386970 C2      4/2010
(Continued)

*Primary Examiner* — Jyoti Nagpaul
(74) *Attorney, Agent, or Firm* — Sherry Womack Austin

(57) ABSTRACT

A cartridge and an associated apparatus for preparing a biological sample includes a reaction chamber configured to be closed by a substrate carrying the biological sample, where the reaction chamber is connected to a fluidic inlet system and a fluidic outlet system. When the substrate closes the reaction chamber, the fluidic inlet system, the reaction chamber, and the fluidic outlet system constitute a fluidic system that is closed to an environment outside the cartridge with respect to an exchange of liquids. Further, a pressure-driven flow through the reaction chamber may be induced by actuation of deformable membranes formed in the cartridge.

13 Claims, 2 Drawing Sheets

(52) U.S. Cl.
CPC ..... *B01L 2200/026* (2013.01); *B01L 2200/10* (2013.01); *B01L 2200/16* (2013.01); *B01L 2400/0487* (2013.01); *B01L 2400/082* (2013.01)

(56) References Cited

U.S. PATENT DOCUMENTS

| | | | |
|---|---|---|---|
| 8,173,068 B2* | 5/2012 | Loeffler | B01L 3/502 422/501 |
| 2002/0109838 A1 | 8/2002 | Columbus | |
| 2004/0254559 A1 | 12/2004 | Tanaami | |
| 2005/0095699 A1 | 5/2005 | Miyauchi | |
| 2006/0034728 A1* | 2/2006 | Kloepfer | A61B 5/14532 422/68.1 |
| 2007/0036679 A1 | 2/2007 | Munenaka | |
| 2008/0056954 A1 | 3/2008 | Loeffler | |
| 2008/0237046 A1 | 10/2008 | Hirahara | |
| 2010/0255471 A1 | 10/2010 | Clarke et al. | |
| 2012/0196320 A1 | 8/2012 | Seibel et al. | |
| 2012/0230886 A1 | 9/2012 | Henry et al. | |

FOREIGN PATENT DOCUMENTS

| | | |
|---|---|---|
| WO | 2011094577 A2 | 8/2011 |
| WO | 2012012458 A1 | 1/2012 |
| WO | 2012067985 A2 | 5/2012 |

\* cited by examiner

CARTRIDGE AND APPARATUS FOR PREPARING A BIOLOGICAL SAMPLE

CROSS-REFERENCE TO PRIOR APPLICATIONS

This application is the U.S. National Phase application under 35 U.S.C. § 371 of International Application No. PCT/IB2013/058789, filed on Sep. 24, 2013, which claims the benefit of U.S. Provisional Patent Application No. 61/736,697, filed on Dec. 13, 2012. These applications are hereby incorporated by reference herein.

FIELD OF THE INVENTION

The invention relates to a cartridge for preparing a biological sample, particularly for staining a sample of tissue or collection of cells. Moreover, it relates to an apparatus for processing such a cartridge.

BACKGROUND OF THE INVENTION

The US 2012/230886 A1 discloses an overlay device with channels on a bottom side that can be placed upon a microscope slide carrying a biological sample. Openings at the ends of the channels allow for the inlet of reagents into said channels at one end and their outlet at the other end. A microscope slide with such an overlay device can be placed into an alignment fixture with inlet ports and outlet ports that are received by the respective openings of the overlay device.

SUMMARY OF THE INVENTION

It would be advantageous to have means that allow for a more robust, simple, and/or user-friendly preparation of a biological sample with reagents, for example with stains that can prepare a complete sample slide in a homogeneous way following complex protocols involving multiple reagents.

According to a first aspect, the above concerns are addressed by a cartridge for preparing a biological sample, for example for staining a sample of tissue or cells for microscopic inspection. The cartridge comprises a cartridge-body with the following components:

a) A reaction chamber with an opening that can be closed by a substrate carrying a sample (on a side facing the reaction chamber);

b) A fluidic inlet system for providing at least one reagent fluid to the aforementioned reaction chamber;

c) A fluidic outlet system for receiving fluid from the reaction chamber.

The above-mentioned components shall be designed such that the fluidic inlet system, the reaction chamber with a substrate closing its opening, and the fluidic outlet system are (hydro-dynamically) interconnected and substantially closed with respect to the exchange of liquids with the environment. With other words, the fluidic inlet system, the reaction chamber, and the fluidic outlet system commonly constitute a fluidic system that is closed to the environment (with respect to liquids) when a substrate closes the reaction chamber.

The term "cartridge" shall denote an element or unit with internal cavities in which a medium can be accommodated for storage, transportation, and/or processing. It will usually be an exchangeable and disposable component which is used only once for a single sample. Preferably, the cartridge is a one-piece component and/or (substantially) consists of a monolithic material. It may for example (substantially) consist of one or several injection molded parts that are permanently attached to each other. Conceptually, the cartridge may comprise the substrate or not. In the latter case, the "cartridge-body" is typically identical to "the cartridge".

The term "reaction chamber" shall denote a cavity in the cartridge, wherein the walls of the cartridge that border this cavity shall conceptually belong to the reaction chamber.

A "fluidic system" shall in general denote any system of cavities (like channels, chambers, valves or the like) through which a medium (particularly a fluid) can be transported and routed.

The fluid received by the fluidic outlet system may particularly comprise reagent fluid that has previously been introduced into the reaction chamber by the fluidic inlet system. The fluidic outlet system may hence be or comprise a waste reservoir in which used reagents and/or other waste chemicals can be stored.

The fluidic inlet system, the reaction chamber, and the fluidic outlet system may optionally be completely closed to the environment when a substrate closes the reaction chamber, i.e. closed with respect to the exchange of fluid (liquid or gaseous). Preferably, some exchange of gaseous media will however be allowable, for example via venting connections to the environment that simplify the design and avoid backpressure build up.

The described cartridge has the advantage to allow for the preparation of a biological sample in a closed system, i.e. in the system comprising nothing but the cartridge and a substrate on which the sample is provided. Closure of this system with respect to the environment prevents any danger of contamination of the sample by the environment as well as of the environment by the sample. This significantly eases the handling of the sample. Additional advantages can be the reduction of reagent consumption, faster reactions due to increased convection in micro-channels, and better reproducibility by the industrial manufacturing of the cartridge including critical reagents.

In general, the substrate may be any (solid) body of material that is suited for carrying a biological sample to be prepared. Most preferably, the substrate will have a plate-like geometry, for example if it is a microscope slide. To allow for the usage of such a plate-like substrate, the opening of the reaction chamber of the cartridge is preferably designed to be closed by a flat surface (of the substrate).

There are several possibilities how the substrate can be attached (or is attached) to the cartridge-body, wherein the attachment must be sufficiently strong to withhold forces occurring during a fluid flow through the reaction chamber.

In one embodiment, the substrate may be attached to the cartridge-body by adhesion and/or gluing, i.e. by material bonding.

In another embodiment, an intermediate vacuum chamber is provided between the substrate and the cartridge-body in which an underpressure can be established, i.e. a pressure below ambient pressure (usually 1 bar). Ambient pressure will therefore squeeze the substrate to the cartridge-body. The underpressure may for example be applied via a duct connecting the vacuum chamber to an instrument. The vacuum chamber is usually different from and hydrodynamically unconnected to the reaction chamber.

In still another embodiment, the substrate may be attached to the cartridge-body by clamping, for example via mechanical springs, and/or by electromagnetic forces, for example generated by (electro-)magnets.

When the substrate closes the opening of the reaction chamber, the internal geometry of the cavity of the reaction chamber is completely determined. In a preferred embodiment, this geometry is such that the height of this reaction chamber cavity above the substrate is less than about 200 µm, preferably less than 100 µm, or most preferably less than about 50 µm. In case of a substrate with a flat surface closing the opening of the reaction chamber, the resulting cavity will have the geometry of a cuboid in which the height is by definition the distance between the substrate and the opposite side of the cuboid. For a more general geometry of the reaction chamber cavity (e.g. when entrance and exit zones will be designed such that a well-defined flow pattern is achieved), the height may be defined as the diameter of the largest sphere that completely fits into said cavity.

A comparatively small height of the reaction chamber of less than about 200 µm or even 100 µm has the advantage that the reagent fluid flowing through the chamber will come into intimate contact with a sample on the substrate by convection during flow, thus increasing the speed of desired reactions like staining, while requiring only small amount of reagents.

At least one spacer element may optionally be disposed between the substrate and the cartridge-body in order to guarantee a desired distance between these elements. The spacer element may for example comprise beads of well-defined diameter that are embedded into a soft connection material, e.g. an adhesive or a glue.

The area covered by the reaction chamber (on the substrate) may be up to about 1 cm$^2$, preferably up to 5 cm$^2$, thus allowing for the accommodation of samples of this size.

The cartridge may preferably comprise at least one control element (e.g. a valve) that allows fluid routing and/or actuation. Additionally or alternatively, it may comprise at least one pumping element for inducing a pressure-driven flow of fluid from the fluidic inlet system through the reaction chamber to the fluidic outlet system. In this context, the term "pressure-driven" shall indicate that there is at least one element or position in the cartridge (e.g. the pumping element) at which a well-defined pressure can controllably be generated, wherein this pressure induces the fluid flow. Accordingly, the ability to control the pressure implies the ability to control fluid flow, particularly within the reaction chamber. This controllability is an advantage with respect to other flow mechanisms (e.g. a gravity driven flow). Moreover, a pressure-driven flow has the advantage to induce a high shear acting on the sample, thus allowing for a close contact between flowing reagents and the sample.

The aforementioned pumping element may for example be realized as an element that can be moved and/or be deformed such that it induces fluid flow, wherein said pumping element is preferably located adjacent to the fluidic inlet system, the reaction chamber, and/or the fluidic outlet system. Such a pumping element may for example be or comprise a deformable or moveable membrane capable of inducing fluid flows. This membrane may constitute a wall in the fluidic inlet and/or the fluidic outlet system, wherein a force acting on said membrane causes a deflection and thus a flow of the fluid in the adjacent fluidic system. The movable and/or deformable pumping element provides a simple means for controlling fluid flow in the cartridge without a need for directly contacting said fluid. A similar flexible membrane can also be incorporated as a valve to route flow in different directions and/or close off certain parts of the fluidic system. Preferably, two or more pumping elements (or valves) of the described kind may be present. Moreover, the pumping element and/or a system comprising the pumping element may operate as a peristaltic pump that induces an oscillating pressure which is converted into a unidirectional fluid flow by other components, particularly (appropriately controlled) valves.

The cartridge may optionally comprise at least one reagent reservoir in which reagents in dry or wet form are provided for a later use when a substrate with a sample is attached. The cartridge may thus be manufactured ready-to-use, freeing the user from the need to handle or contact (potentially sensitive and/or toxic) reagents. The reagent reservoir is preferably sealed or sealable with respect to the cavity (e.g. the reaction chamber) it is disposed in.

In a preferred embodiment, the aforementioned reagent reservoir comprises at least one stain and/or fixative for preparing a biological sample. The cartridge can then be used to prepare a biological sample for microscopic inspection.

The substrate may conceptually be considered as belonging to the cartridge or as an element separate from the cartridge. Typically, the cartridge without the substrate will be a component of its own that can be combined with a substrate which is produced separately and which can be used for other purposes, too (e.g. if the substrate is a microscope slide). In either case, the substrate may be transparent in order to allow for a visual inspection of the sample in the reaction chamber or afterwards. Preferably, such a transparent substrate has a low thickness of less than about 0.2 mm, thus facilitating a direct visual inspection with a microscope at high resolution.

In another embodiment, the substrate may carry at least one marker, for example a sign (like a cross) that is printed or etched onto its surface, wherein said marker can be localized by any external detector. This allows for a precise localization and/or alignment of a sample provided on the substrate with respect to the cartridge or another apparatus. Features can be present on the substrate that assist in controlling the height of the reaction chamber upon closure.

According to a further embodiment, the cartridge comprises at least one identifier that can be identified by an external detector. In this context, the term "identifier" shall denote an element representing a symbol or a code that contains information about the identity and/or about properties of the substrate and/or the sample carried by the substrate. The identifier may for example be an RFID tag or a 2D barcode containing data about the type of cartridge and reagents, sample (type of tissue, name of patient, etc.).

In another optional embodiment, the cartridge may comprise at least one indicator for indicating the status of a reagent and/or a reaction in the fluidic inlet system, the reaction chamber, and/or the fluidic outlet system. The indicator may for example be a sensor or a dye that changes its color depending on parameters like temperature or pH value. Likewise also an instrument that uses the cartridge can contain means of monitoring the progress of the reactions inside the cartridge by monitoring for instance the transmission or reflection of light in a reagent reservoir or the reaction chamber.

According to another aspect of the invention, the concerns with respect to the state of the art are addressed by a processing apparatus comprising the following components:

a) An interface to which a cartridge of the kind described above can be coupled (i.e. a cartridge with a reaction chamber that can be closed by a substrate, a fluidic inlet system, and a fluidic outlet system, wherein said chamber with a substrate and said systems are closed with respect to the exchange of liquids with the environment);

b) At least one actuator for controlling the processing of the sample in a cartridge when it is coupled to the aforementioned interface.

A cartridge according to this embodiment of the invention provides a closed system around an entire sample and the necessary reagents for preparing the sample. In case the preparation of the sample requires more manipulations than just exposing it to appropriate reagents, these steps can be executed with the help of the actuator(s) of the above processing apparatus.

The cartridge and the processing apparatus may be designed such that the fluidic system of the cartridge (with reaction chamber, fluidic inlet system, and fluidic outlet system) can reversibly be connected to a fluidic system in the apparatus. Then certain reagents can be provided by the apparatus to the cartridge via these reversible interconnections.

The cartridge and the apparatus are different realizations of the same inventive concept, i.e. the preparation of a sample in a system that is closed by attachment of a substrate carrying the sample. Explanations and definitions provided for one of these realizations are therefore valid for the other realization, too.

The actuator(s) of the processing apparatus may for example comprise at least one thermal controller for controlling the temperature in the reaction chamber of a cartridge when the latter is attached to the interface. A control of temperature is often helpful or even necessary in order to enable (bio-)chemical reactions and/or to protect a sample from damages or to stabilize it. Thermal control can be achieved via contact to elements of a preset temperature and/or via heat transfer by radiation.

Additionally or alternatively, the actuator(s) may comprise at least one pressure controller for controlling the fluid flow in a cartridge attached to the interface of the apparatus. The pressure controller may for example comprise an element that acts on a movable and/or deformable pumping element of a cartridge as described above. Most preferably, there are one or more such actuators which cooperatively control pressure in the fluidic inlet system and in the fluidic outlet system, thus allowing for well-defined flow conditions in the intermediate reaction chamber.

According to another embodiment, the processing apparatus may comprise one or more optical investigation means, e.g. an optical window, for characterizing the sample in the cartridge and/or allowing an inspection of the reaction chamber of a cartridge coupled to the interface of the apparatus. Thus reactions taking place in the cartridge can be monitored in real time. In addition such windows allow examination of the sample after a staining reaction without removing the sample from the cartridge.

The invention further relates to the use of a cartridge or an apparatus of the kind described above for sample preparation and/or specific staining in histopathology, cytopathology, immunohistochemistry and in-situ hybridization, in particular for oncology applications for patient stratification based on identification of molecular changes in cancer cells. The preparation may particularly comprise the dewaxing, rehydration, antigen retrieval, denaturation, staining and/or the fixation of the sample. The sample may comprise tissue sections (freshly frozen, formalin fixed, formalin fixed— paraffin embedded) and/or cell agglomerates (spin-down, stamped or otherwise immobilized and fixed).

The invention further relates to the use of a cartridge or an apparatus of the kind described above for a combined sample preparation and microscopic analysis of a biological sample in histopathology, cytopathology, immunohistochemistry and in-situ hybridization.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
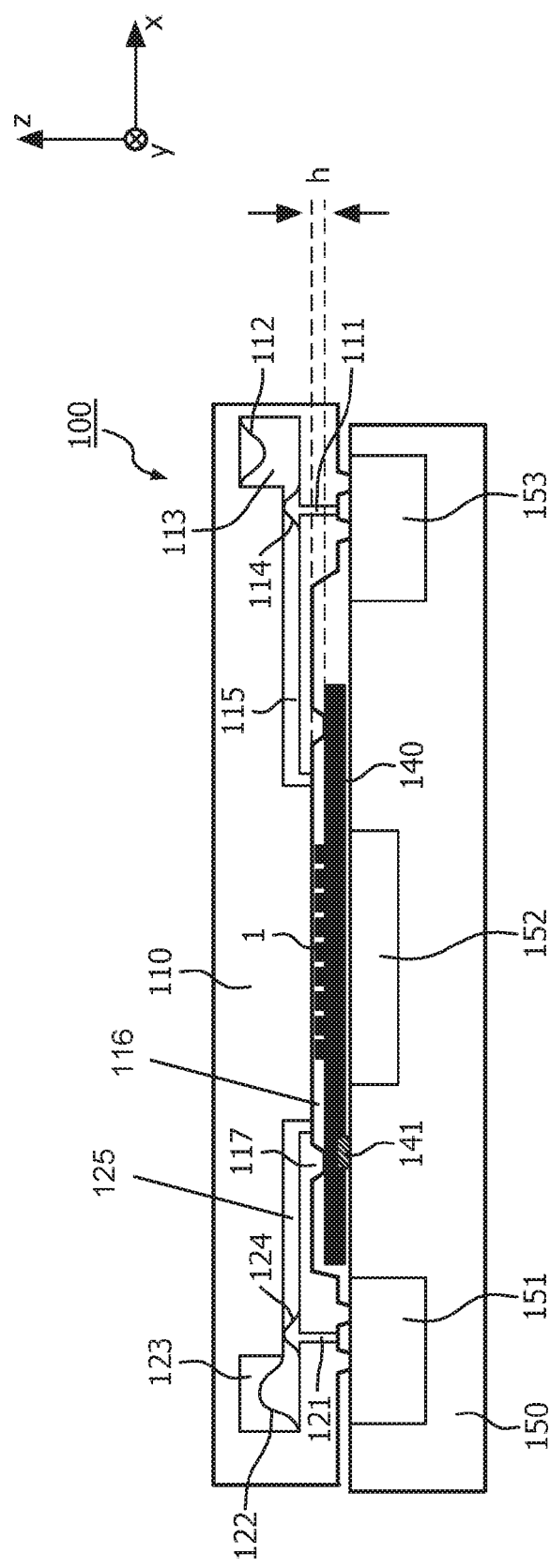
FIG. 1 shows a cartridge attached to an apparatus in accordance with an embodiment of the invention.

Pathology diagnostic investigation of patient material (e.g. tissue and cells) is the basis of many treatment decisions, in particular in oncology. Standard, thin slices from a biopsy are presented on microscope slides and stained according to certain protocols to visualize the morphology of the tissue, e.g. by Hematoxylin-Eosin (H&E). Moreover, in situ staining for disease-specific biomarkers can be used for companion diagnostics of targeted drugs, based on the specific binding of antibodies to proteins present on the tissue, so-called immunohistochemistry (IHC), and hybridization of designed sequences of nucleotides to parts of chromosomes or genes, or messenger-RNA (in-situ hybridization, ISH). Assessment generally occurs with a bright field or a fluorescence microscope, or a digital scanner. Slides need to be stored after investigation for a long period as back-up in case the diagnosis needs to be re-assessed.

Tissue samples may be obtained by cutting a thin section of about 2-8 microns from a paraffin-embedded biopsy. The so-called coupes are placed on a microscope glass slide on a water film to relax from the microtomic strain and are then left to dry. There are a number of staining protocols available for different applications. Staining protocols can be carried out on the bench manually by dipping the slide with the coupe in different solutions containing the reagents (a typical protocol is listed below). Staining protocols typically take at least 2.5 hours; in some cases over-night incubation is required. The flow of reagents can be driven by interfacial and gravitational forces in the (semi-)open systems which limits the control and flow rates.

Staining procedures according to the state of the art often suffer from the following drawbacks:

Inefficient use of equipment due to batch operation.

Inefficient use of reagents due to limited shelf life of stored reagents at low usage.

Risk of failure due to open access to reagents and protocols.

High maintenance effort for liquid interfaces and contamination due to open system.

Limited control over fluid flow leading to long assay times and inhomogeneity of staining Lack of standardization/external approval.

To address these issues a new way of executing histological and cytological staining protocols is proposed. According to an embodiment of this approach, a sample is placed on a substrate that is part of a cartridge that is closed hermetically after introduction of the sample. A closed "reaction chamber" is created with a narrow gap of the order of about 50 microns. The cartridge can optionally be placed on an apparatus or instrument that controls the temperature of the reaction chamber and the flow of the reagents, preferably via pneumatic interfaces. Reagents may be pumped into the reaction chamber and over the sample by a pressure-driven flow in closed channels. This allows a precise control of flow conditions, limits the amount of reagents, and improves the washing and reagent replacement steps. This leads to much faster execution of the protocols and a more reproducible result. Reagents can be placed on board of the cartridge. The cartridge may be a disposable. The sample can optionally be inspected without removal from the cartridge due to an optical window which is present in the sample chamber. With epi-fluorescence the sample can be inspected through the substrate (if transparent); for brightfield, also a window must be present on the opposite side of the substrate to allow transmission measurement.

FIG. 1 schematically shows a sectional side view of a cartridge 100 that is attached to the interface (planar top surface) of a processing apparatus 150 according to an embodiment of the above principles.

The cartridge 100 is preferably comprised of a one-piece cartridge-body 110 that can for example be made by injection molding (e.g. of two or more parts that are permanently attached to each other). The cartridge has on its bottom side (in the Figure) a cavity which is called "reaction chamber" 116 in the following and which has a substantially flat, cuboid-shaped geometry with a height h of less than about 100 µm. The area of the reaction chamber in the x, y-plane may be up to several $cm^2$. The side walls of the reaction chamber 116 are formed by protrusions or rims 117 that end in a common plane, thus defining a closed curve around a bottom opening of the reaction chamber in said plane. This bottom opening of the reaction chamber 116 is closed and sealed in the shown example by a substrate 140. Attachment between the cartridge-body 110 and the substrate 140 can for example be achieved by and adhesive or glue on top of the rims 117 (alternative possibilities are discussed with respect to FIG. 2).

The aforementioned substrate 140 may for example be a microscope slide by which a biological sample 1 to be processed or prepared can be provided. The sample 1 is located on the top side of the substrate 140 and thus faces the interior of the reaction chamber 116. The substrate 140 may conceptually be considered as belonging to the cartridge 100 or as a separate element of its own. In another preferred embodiment the substrate is made of an amorphous polymer, optionally provided with coating layers for the desired surface properties for tissue adhesion and/or barrier properties and/or anti-reflection properties. In a preferred embodiment the substrate is an integral part of the cartridge that can be connected permanently via hinges to the cartridge.

The cartridge 100 further comprises a fluidic inlet system that is hydrodynamically coupled to the reaction chamber. In the shown example, the fluidic inlet system comprises a reagent reservoir 113 in which reagents (e.g. stains) needed for the processing of the sample 1 are stored. The reagent reservoir 113 is connected to a first end of the reaction chamber 116 by a channel 115. One side wall of the reagent reservoir 113 is formed by a deformable membrane 112 that acts as a movable wall of the reagent reservoir 113, allowing for a volume change (due to the outflow of reagents) while keeping the fluidic system closed with respect to the environment. The membrane 112 may be suspended with an elastic tension, or it may be provided with sufficient area to be relaxed in both the filled and the empty state of the reagent reservoir 113.

Another membrane 114 is disposed at one wall of the channel 115. The outside of this membrane 114 is connected via a conduit 111 to the bottom side of the cartridge 100.

The cartridge 100 further comprises a fluidic outlet system that is connected to a second end of the reaction chamber (opposite to the first end). The fluidic outlet system comprises a waste chamber 123 and a channel 125 connecting said chamber to the second end of the reaction chamber 116. One wall of the waste chamber 123 is optionally constituted by a deformable membrane 122. Similar to the membrane 112 in the reagent chamber 113, this deformable membrane 122 allows for a changing filling level of the waste chamber 123 while keeping the fluidic system isolated from the environment. Furthermore, another flexible membrane 124 may be disposed in the outlet channel 125, the outside of said membrane being connected to the bottom side of the cartridge by a conduit 121.

When a substrate 140 with a sample 1 is attached to the opening of the reaction chamber 116 of the cartridge, the rims 117 of the opening tightly contact the substrate in a sealed manner (e.g. being attached by gluing), thus forming a closed fluidic system around the sample 1. This fluidic system comprises the fluidic inlet system, the reaction chamber, and the fluidic outlet system and allows for a controllable, pressure-driven flow of reagent fluid from the reagent reservoir 113 through the reaction chamber 116 into the waste chamber 123.

In order to allow for a control of the aforementioned fluid flow, the cartridge 100 with the substrate 140 is coupled to a processing apparatus or instrument 150 at an interface of said apparatus. In the shown embodiment, said interface is substantially a flat surface on which the substrate 140 and the cartridge 100 can be placed.

When the cartridge 100 is on the instrument, the substrate is located above a thermal controller 152 of the apparatus 150 by which the temperature in the reaction chamber 116 can be controlled. Moreover, the conduits 111, 121 leading to the membranes 114 and 124 of the fluidic inlet system and fluidic outlet system, respectively, are located above pneumatic controllers 151 and 153. When the pneumatic controller 153 on the right hand side of the apparatus 150 generates an overpressure, this pressure is conveyed by the conduit 111 to the membrane 114 which bulges inwardly into the inlet channel 115, thus creating a flow of reagents towards the reaction chamber 116. Preferably, the membrane 114 is part of a peristaltic pump comprising additional elements such as valves (not shown) in order to convert an oscillating pressure into a fluid flow directed to the reaction chamber. The membrane is hence an actuator that is deflected in one or the other direction depending on the pressure difference between the one side and the other side of the actuator. By applying underpressure (typical 0.1-0.2 bar) the membrane is deflected in the direction of the low pressure side, by applying overpressure (typical 1.5 to 2.0 bar) in the opposite direction.

Similarly, the pneumatic controller 151 on the left hand side of the apparatus 150 can act via the conduit 121 on the membrane 124, which induces a (peristaltic) flow of (waste) fluid into the waste chamber 123.

The membranes 114 and 124 hence act as pumping elements with which a well controlled pressure-driven flow of fluids can be generated in the reaction chamber 116.

It should be noted that the membranes 112 and 122 in the reagent reservoir 113 and the waste chamber 123, respectively, are fixed at different positions and thus initially (without external pressure) in different states: The membrane 112 of the reagent reservoir 113 is fixed remote from the channel 115 such that reagent fluid can completely fill the reagent reservoir 113 in the initial state of the membrane. In contrast to this, the membrane 122 in the waste chamber 123 is fixed at the entrance of the channel 124 such that the waste chamber is substantially empty in the initial state of the membrane.

Moreover, the fluidic inlet system may optionally comprise several reagent reservoirs that can independently be emptied into the reaction chamber.

Figure 2:
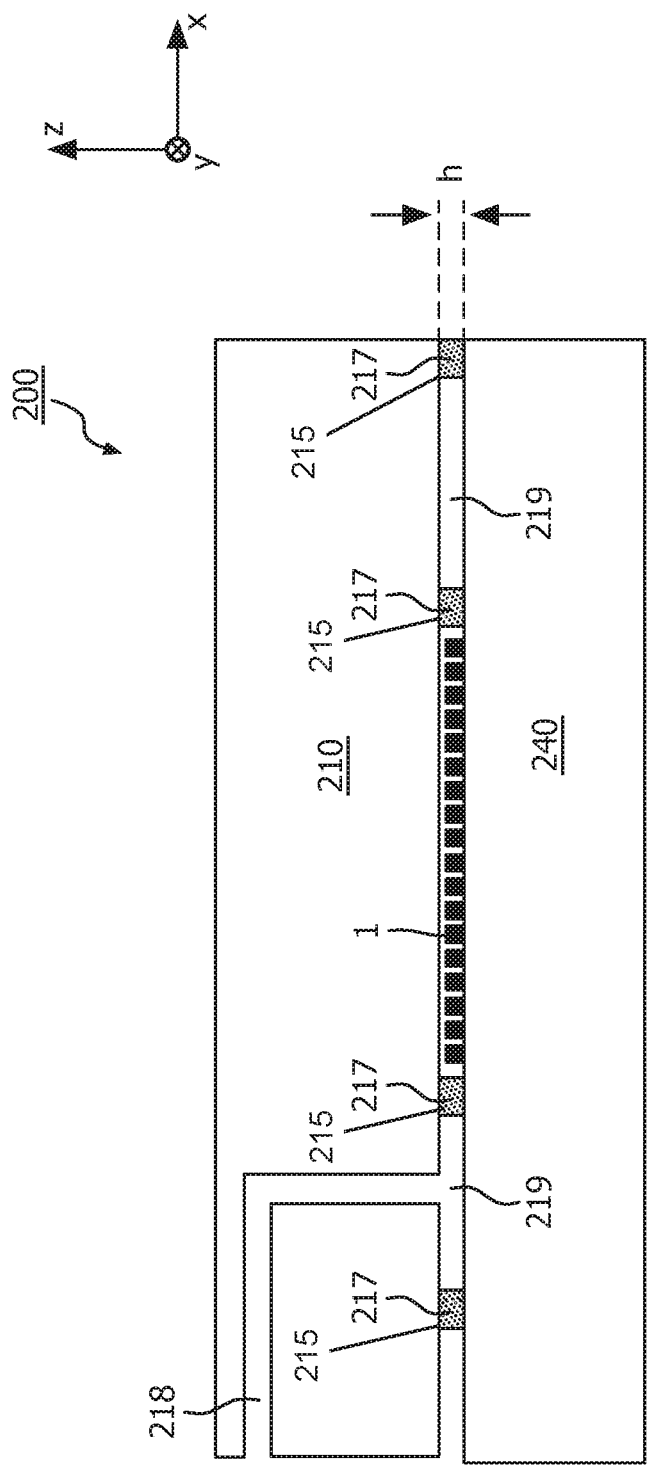
FIG. 2 shows an embodiment for the fixation of the substrate to the cartridge.

FIG. 2 illustrates in a schematic side view an alternative approach for the attachment of a substrate 240 (e.g. a microscope slide) to a cartridge-body 210. Details of the fluidic systems in the cartridge 200 may be similar as in FIG. 1 and are therefore omitted in the drawing for clarity.

In the shown embodiment, attachment of the substrate 240 to the cartridge body 210 is achieved by providing a vacuum chamber 219 between the substrate 240 and the cartridge body 210. This vacuum chamber 219 is defined around the sample 1 by (e.g. sticky or glued) concentric ridges 217. The gap height h between substrate 240 and the cartridge body 210 can optionally be controlled by introducing spacers 215 (e.g. glass beads) of precisely defined diameter (these can be part of the glue if glue is used).

Moreover, a suction channel 218 is provided in the cartridge-body 210 which connects the vacuum chamber 219 to the outside of the cartridge and/or to a pressure controller (not shown). Thus an underpressure of for example about 0.1-0.2 bar can be applied to the vacuum chamber 219 which generates a tight attachment of the substrate 240 to the cartridge-body 210.

The strength of the attachment between substrate and cartridge-body must be higher than the force exerted by the pressure-driven flow in the reaction chamber. In the case of using vacuum this means that the product of the pressure and the surface area in the vacuum part must equal that in the reaction chamber, provided that the substrate and cartridge are stiff. With glue the strength of the glue times the contact surface of the glue ridge must equal the force of the liquid in the reaction chamber.

Clamping of the substrate to the cartridge-body is yet another option. This can be done by spring loading or by (electro-)magnets that can be part of the instrument (150 in FIG. 1) in which the cartridge is processed.

An essential feature of the described embodiments is the fact that the sample is introduced in a closed chamber with only one micro-fluidic inlet and outlet port, both perpendicular (out of the plane) of the substrate that holds the sample (e.g. tissue or cytology material). The reagents are pumped over the sample by a pressure-driven flow which allows a higher shear rate than in semi-open systems. The increased shear rates allow a faster supply and penetration of reagents and a more efficient washing, which leads to improved staining quality at reduced time.

There is a large number of (optional) features which can be part of this approach, for example:

The sample can be presented on a separate flat substrate, like a microscope slide, or alternatively a plastic substrate. The size of the sample is typically of the order of about 1 cm$^2$ to 2 cm$^2$.

The substrate thickness can be equal to that of conventional slides (1 mm) to be compatible with existing solutions, or preferably be much thinner (e.g. smaller than about 0.2 mm) to enable inspection through the substrate at high resolution and make cover slides obsolete.

The substrate can contain features ("markers") which allow a precise and reproducible placement of the sample to facilitate optical inspection after staining. In FIG. 1, one such marker 141 is schematically indicated.

As shown, the substrate can be a separate part which after introduction in the cartridge is attached e.g. by gluing or clamping. Alternatively, the substrate can be an integral part of the cartridge. A cartridge opening or lid can be present that allows introduction of the sample and can be closed after sample introduction. The substrate with sample can be removed after processing from the rest of the cartridge for efficient storage.

Reagents can be stored in wet and/or dry form on the cartridge in separate sealed compartments, in particular the assay-specific, costly stains and optionally the environmentally harmful substances. Separate reagent containers can be attached to the cartridge to allow for more flexibility in logistics and storing conditions.

The waste of reagents can be collected on board of the cartridge so that no wet contamination occurs on the apparatus and no cleaning is necessary. The waste container can be designed as detachable entity to facilitate disposal.

One or more additional windows can be present in the cartridge, e.g. opposite to the substrate to enable optical inspection of the sample in transmission mode, or inspection through the extra window instead of the substrate.

A fixative can be introduced in the last step to preserve the sample for improved stability and contrast during inspection.

The fluid driving can be done via pneumatic actuators that act on membranes inside the cartridge. In this way no direct contact of liquids with the instrument is possible.

The cartridge can contain one or more identification means, like a barcode or RFID chip that recognizes the type and/or reagents present. In addition an ID can be present on the substrate in case the sample is introduced on a separate substrate.

The cartridge can contain indicators for the status of reagents and the status of the reaction.

The cartridge and the apparatus can be designed to allow having reagent storage on the apparatus as well (e.g. for simple buffers), wherein said reagents can be transferred into the cartridge via closable interconnections (not shown).

Example

In the following, an exemplary staining procedure will be described in more detail. In this procedure, FISH (fluorescence in situ hybridization) was performed on a prototype cartridge using a Kreatech protocol (Kreatech Diagnostics, Amsterdam), with a 50 μm gap reaction chamber and an incubation time of 3.5 hrs (to make two protocols a day possible). To check whether this will lead to successful FISH, a manual protocol using the same incubation time was also performed.

Cells from an SKBR3 cell line were cytospun on slides and stored at −80° C. The cell collections on the slide were treated as follows:

fixed in 4% formaldehyde for 10 min;
washed in PBS;
washed in demi H$_2$O;
completely dried on a microscope slide;
a tape was applied to the cartridge;
the microscope slide was applied to the tape.

The following Table 1 summarizes the steps that were executed on the achieved cartridge setup on a first day (temperatures are as set by the instrument):

TABLE 1

| Step | TEMP (° C.) | Time (s) | Pump/Incubate | Reagent |
|---|---|---|---|---|
| 1 | RT | 30 | Pump | (MES) buffer |
| 2 | 94 | 480* | Incubate | (MES) buffer |
| 3 | 38 | 30** | Pump | (MES) buffer |

TABLE 1-continued

| Step | TEMP (° C.) | Time (s) | Pump/Incubate | Reagent |
|---|---|---|---|---|
| 4 | 38 | Until t = ~38° C. | Incubate | (MES) buffer |
| 5 | 38 | 30 | Pump | 2 × SSC/0.5% igepal |
| 6 | 38 | 900 | Incubate | 2 × SSC/0.5% igepal |
| 7 | RT | 30 | Pump | 70% Ethanol |
| 8 | RT | 30 | Pump | 85% Ethanol |
| 9 | RT | 30 | Pump | 100% Ethanol |
| 10 | RT | 30 | Incubate | 100% Ethanol |
| 11 | RT | AIRDRY | AIRDRY | AIR |
| 13 | RT | 3.5 (2 pump strokes) | Pump | Probe mix |
| 14 | 83 | 450 | Incubate | Probe mix |
| 15 | 38 | 86400 (24 h) | Incubate | Probe mix |
| 16 | 38 | 30 | Pump | 0.4 × SSC/0.3% igepal |
| 17 | 75 | 240*** | Incubate | 0.4 × SSC/0.3% igepal |
| 18 | RT | 15 | Pump | 2 × SSC/0.1% igepal |
| 19 | RT | 30 | Pump | 70% Ethanol |
| 20 | RT | 30 | Pump | 85% Ethanol |
| 21 | RT | 30 | Pump | 100% Ethanol |
| 22 | RT | 30 | Incubate | 100% Ethanol |
| 23 | RT | until dry | air dry | air |

(*it takes about 180 s to reach 94° C.)
(**pump to make reaction chamber cool faster, remove bubbles)
(***it takes about 2 minutes to reach this temperature)
(RT = room temperature)

After this, the following steps were executed:
the microscope slide was removed from the cartridge;
the tape was removed from microscope slide;
it was made sure that sample and glass are completely dry;
a small drop (10-20 µl) of DAPI containing mounting fluid was applied;
a cover slip was applied;
after 10 min, the sample was imaged.

The experiment proved that the resulting fluorescence images showed FISH signal.

In summary, an embodiment of a new device was described which allows the automated staining of biological samples from patients, in particular tissue sections. The sample can be introduced in the form of a microtomed section of a freshly frozen or formalin fixed, paraffin embedded biopsy or as a spun-down cell suspension. After introduction the cartridge is closed such that a completely closed compartment is defined around the sample with well controlled narrow gap. One side of the compartment is determined by a thin transparent substrate to allow optical inspection of the sample in closed state. Access for fluids is provided via entrance and exit ports in the compartment. Different treatment protocols can be carried out by actively pumping reagents and washing solutions over the sample in the compartment. In a preferred embodiment reagents are stored on board of the cartridge and the fluids are actuated pneumatically. Pneumatic actuators are preferably situated next to the compartment to allow a flat and low-cost design. The cartridge can be composed of a combination of injection-molded and/or vacuum-formed plastic parts and flexible membranes and optionally with metal elements and glass substrate elements. Specific optical properties can be adjusted to achieve for instance protection of sensitive chemicals, organic and/or inorganic barrier layers can be present to achieve the necessary shelf life of the cartridge and reagents, heat absorbing and/or conducting elements can be introduced.

The invention can be applied in histopathology, and cytopathology for carrying out immunohistochemistry, proximity ligation assays, padlock probe assays and in-situ hybridization to DNA and/or RNA, or other biological assays for brightfield and/or fluorescence-based inspection, of tissue sections and/or cell agglomerates (spin-down); in particular for oncology applications for patient stratification based on identification of molecular changes in cancer cells and companion diagnostics.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A cartridge for processing a sample carried on a substrate, the cartridge comprising:
    a cartridge body comprising:
        a reaction chamber;
        walls that surround the reaction chamber and define an opening extending between the walls and across the reaction chamber;
        a fluidic inlet system configured to provide at least one reagent fluid to the reaction chamber;
        a fluidic outlet system configured to receive fluid from the reaction chamber; and
        corresponding pump membranes positioned in the fluidic inlet system and the fluidic outlet system, wherein the corresponding pump membranes are configured to induce a pressure-driven fluid flow from the fluidic inlet system through the reaction chamber to the fluidic outlet system;
    wherein the fluidic inlet system, the reaction chamber, and the fluidic outlet system are configured to be closed to an exchange of liquids with an environment outside the cartridge by the walls of the cartridge body and a wall of the substrate carrying the sample in response to an attachment of the substrate carrying the sample over the walls of the cartridge body and the opening.

2. The cartridge according to claim 1, wherein the wall of the substrate comprises a flat surface and the opening of the reaction chamber is configured to be closed by the flat surface with at least a portion of the flat surface being positioned inside an interior of the reaction chamber after the attachment of the substrate carrying the sample.

3. The cartridge according to claim 1, wherein the cartridge body comprises at least one of an adhesive, a glue, an intermediate vacuum chamber, and a source of electromagnetic forces, configured to provide the attachment of the substrate carrying the sample.

4. The cartridge according to claim 1, wherein a height of the reaction chamber above the substrate carrying the sample closing the opening is less than about 50 μm.

5. The cartridge according to claim 1, further comprising spacers disposed between the substrate carrying the sample and the cartridge body, with each spacer spaced apart from each other spacer.

6. The cartridge according to claim 1, wherein the corresponding pump membranes are configured to be at least one of moved and deformed to induce the pressure-driven fluid flow.

7. The cartridge according to claim 1, wherein the fluidic inlet system comprises at least one reagent reservoir filled with the at least one reagent fluid, wherein said reservoir is sealed from the environment outside the cartridge.

8. The cartridge according to claim 1, further comprising at least one of a marker configured to be localized by an external detector and an identifier configured to be identified by an external detector.

9. The cartridge according to claim 1, further comprising at least one indicator configured to indicate a status of at least one of a reagent and a reaction.

10. The cartridge according to claim 1, further comprising a control element configured to route a fluid from the fluidic inlet system through the reaction chamber to the fluidic outlet system.

11. The cartridge according to claim 1, wherein at least one of the fluidic inlet system and the fluidic outlet system is completely arranged within an interior of the cartridge body between a top surface and a bottom surface of the cartridge body.

12. The cartridge according to claim 1, wherein the corresponding pump membranes are configured to be at least one of moved and deformed to induce the pressure-driven fluid flow.

13. A cartridge for processing a sample carried on a substrate, the cartridge comprising:
   a cartridge body comprising:
      a reaction chamber;
      walls that surround the reaction chamber and define an opening;
      a fluidic inlet system configured to provide at least one reagent fluid to the reaction chamber;
      a fluidic outlet system configured to receive fluid from the reaction chamber; and
      corresponding pump membranes positioned in the fluidic inlet system and the fluidic outlet system, wherein the corresponding pump membranes are configured to induce a pressure-driven fluid flow from the fluidic inlet system through the reaction chamber to the fluidic outlet system, and
   wherein the fluidic inlet system, the reaction chamber, and the fluidic outlet system are configured to be closed to an exchange of liquids with an environment outside the cartridge by the walls of the cartridge body and a wall of the substrate carrying the sample in response to an attachment of the substrate carrying the sample over the opening.

* * * * *